United States Patent [19]

Kang et al.

[11] Patent Number: 5,840,542
[45] Date of Patent: Nov. 24, 1998

[54] METHOD FOR MANUFACTURE OF PROINSULIN WITH HIGH EXPORT YIELD

[75] Inventors: Yup Kang, Soowon, Rep. of Korea; Ji-Won Yoon, Calgary, Canada

[73] Assignee: Mogam Biotechnology Research Institute, Kyonggi-do, Rep. of Korea

[21] Appl. No.: 508,664

[22] Filed: Jul. 28, 1995

[51] Int. Cl.$^6$ ..................................................... C12N 15/17
[52] U.S. Cl. .................... 435/69.4; 435/252.33; 530/303
[58] Field of Search ................................. 435/69.1, 69.4, 435/252.33; 530/303

[56] References Cited

U.S. PATENT DOCUMENTS

| | | | |
|---|---|---|---|
| 4,916,212 | 4/1990 | Markussen et al. | 530/303 |
| 5,399,490 | 3/1995 | Balganesh et al. | 435/69.8 |
| 5,460,954 | 10/1995 | Lee et al. | 435/69.5 |

OTHER PUBLICATIONS

Kang, Y. and J.–W. Yoon, Development a High–Expression Vector (PYK10–9) of Human Proinsulin Gene, Biotech. Lett., 13(10):755–760(1991).

Humbel, R.E., Insulin–like Growth Factors I and II, Eur. J. Biochem., 190:445–462 (1990).

Josephson, S. and R. Bishop. Secretion of Peptides from *E. coli*: A Production System for the Pharmaceutical Industry, TIBTECH, 6:218–224 (1988).

Eun, H.M. et al., An Efficient and Site–Specific Gene Trimming Method, Bio Techniques, 7(5): 506–510 (1989).

Fujishige, A. et al., Correct Folding of α–Lytic Protease Is Required for Its Extracellular Secretion from *Escherichia coli*, J. Cell Biol., 118(1):33–42(1992).

Chan, S.J. et al., Biosynthesis and Periplasmic Segregation of Human Proinsulin in *Escherichia coli*, Proc. Natl., Acad. Sci., USA, 78(9):5401–5405(1981).

Laemmli, U.K., Cleavage of Structural Proteins during the Assembly of the Head of Bacteriophage T4, Nature, 227:680–685(1970).

Nilsson, B. et al., Secretion Incompetence of Bovine Pancreatic Trypsin Inhibitor Expressed in *Escherichia coli*, J. Biol. Chem., 266(5):2970–2977(1991).

Thim, L. et al., Secretion and Processing of Insulin Precursors in Yeast, Proc. Natl. Acad. Sci., USA, 83:6766–6770(1986).

Yoon, J.–W. et al., Genetic Differences in Susceptibility of Pancreatic β–Cells to Virus–Induced Diabetes Mellitus, Nature, 264:178–180(1976).

Talmadge, K. et al., An 'Internal' Signal Sequence Directs Secretion and Processing of Proinsulin in Bacteria, Nature, 294:176–178(1981).

Kodadek, T. and M.L. Wong, Homologous Pairing in Vitro Initiated by DNA Synthesis, Biochem. Biophys. Res. Comm., 169(1):302–309(1990).

Schroer, J.A. et al., Mapping Epitopes on the Insulin Molecule Using Monoclonal Antibodies, Eur. J. Immunol., 13:693–700(1983).

Kang, Y. and J.–W. Yoon, Effect of Modification of Connecting Peptide of Proinsulin on Its Export, J. Biotech., 36:45–54(1994).

*Primary Examiner*—Marianne P. Allen
*Attorney, Agent, or Firm*—Darby & Darby

[57] ABSTRACT

The present invention provides a method for manufacture of proinsulin with high export yield, by modifying the connecting peptide region of the proinsulin. According to the method of the present invention, the highest export yield of proinsulin can be obtained, when its connecting peptide region is similar in size to that of human insulin-like growth factor I(hIGFI) or when most of the connecting peptide region of the proinsulin is deleted.

4 Claims, 3 Drawing Sheets

METHOD FOR MANUFACTURE OF PROINSULIN WITH HIGH EXPORT YIELD

FIELD OF THE INVENTION

The present invention relates to a method for manufacture of proinsulin, more specifically, to a novel method for manufacture of proinsulin with high export yield, by modifying the connecting peptide region of the proinsulin.

BACKGROUND OF THE INVENTION

It has been known that the yield of recombinant proinsulin in the course of intracellular expression, is inversely proportional to the size of the expressed fusion peptide. To the present, the addition of a short homologous amino acid gene, [Thr]$_6$, to the 5'-end of the proinsulin gene, to protect against degradation of the expressed proinsulin, resulted in the highest yield of proinsulin in *E. coli*, when the expression of the fused proinsulin gene was efficiently controlled under a strong lambda P$_R$ promoter and a lac ribosome binding site(see: Kang, Y. et al., Biotechnol. Lett., 43:755–760 (1991)). However, purification and refolding of the intracellularly expressed proinsulin has essentially entailed very complex and time-consuming processes, which results in a very low recovery of correctly folded proinsulin.

In this regard, a variety of secretion systems have been employed to resolve these problems; and, there have been several reports on the secretion of rat human proinsulin using a β-lactamase promoter, ribosome binding site, and signal sequence in *E. coli*(see: Talmadge, K. et al., Nature, 294:176–178(1981)). However, the yield of secreted proinsulin was very low in all cases(less than 2–9 ng/mg whole protein), as compared to that of intracellularly expressed proinsulin(see: Kang, Y. et al., Biotechnol. Lett., 43:755–760(1991)). Accordingly, other hosts including Bacillus(see: Novikov, A. A. et al., Biochem. Biophys. Res. Commun., 169:297–301(1990)), Streptomyces(see: Koller, et al., Bio/Technology, 7:1055–1059(1989)) and Saccharomyces(see: Thim, L. et al., Proc. Natl. Acad. Sci., USA, 83:6766–6770(1986)) were also employed to improve the secretion yield of proinsulin using a signal sequence-mediated secretion mechanism. The yield of proinsulin was somewhat increased, compared to that in an *E. coli* system, but was still lower than that of intracellularly expressed proinsulin.

In attempts to further increase the yield, the signal sequence was modified(see: Stahl, S. J. et al., Gene, 71:147–156(1988)) or a different strong promoter or ribosome binding site was introduced(see: Emerick, A. W. et al., Bio/Technology, 2:165–168(1984)), however, the secretion yield was not significantly affected(see: Stader, J. et al., Methods Enzymol., 185:166–187(1991)). Accordingly, the application of secretion systems to the manufacture of proinsulin has been hampered by the low secretion efficiency and the instability of the secreted proinsulin, in spite of its distinct advantages to the system such as a simple purification, correct folding and correct N-terminal processing(see: Stader, J. et al., Methods Enzymol., 185:166–187(1991)).

Under the circumstances, the staphylococcal protein A(hereinafter, referred to as "SPA") fusion expression/secretion system has been known to be a good secretion system for human insulin-like growth factor I(hIGFI) in *E. coli*, in terms of yield, stability, and folding(see: Nilsson, B. et al., Methods Enzymol., 198:3–17(1991); Josephson, S. et al., Trends Biotechnol., 6:218–224(1988)). Furthermore, it has been known in the art that human proinsulin shares a high similarity in amino acid sequence and a similar three-dimensional structure with the hIGFI(see: Humbell, R. E., Eur. J. Biochem., 190:445–462(1990)).

Moreover, it is also postulated that minor changes in amino acids can modulate the folding rate, and that differences in folding kinetics can affect the export(see: Fujishige, A. et al., J. Cell. Biol., 118:33–42(1992); Goldenberg, D. P., Trends Biochem. Sci., 17:257–261(1992); Nilsson, B., et al., J. Biol. Chem., 266:2970–2977(1991)), while the precise mechanism underlying the effect is not understood. Interestingly, earlier studies showed that: the connecting peptide region of proinsulin, may play a role as the nucleation centre of proinsulin folding(see: Snell, C. R. et al., J. Biol. Sci., 250:6291–6295(1975)) and can affect the folding rate of proinsulin(see: Blundell, T. L. et al., Adv. Protein Chem., 26:279–402(1972)). Therefore, the inventors hypothesized that differences in the length of the connecting peptide may increase or decrease the efficiency of translocation by changing the folding rate of the synthesized proinsulin. In this connection, the present inventors have made efforts on the elucidation of whether modification of the connecting peptide region of proinsulin has any effect on the export yield of proinsulin in the SPA fusion expression/secretion system.

SUMMARY OF THE INVENTION

In accordance with the present invention, the inventors obtained the highest export yield of proinsulin by employing the staphylococcal protein A(SPA) fusion expression/secretion system, when its connecting peptide region is similar in size to that of hIGFI or when most of the connecting peptide region of the proinsulin is deleted.

A primary object of the invention is to provide a method for manufacture of proinsulin with high export yield, by modifying the connecting peptide region of the proinsulin.

BRIEF DESCRIPTION OF THE DRAWINGS

The above and the other objects and features of the present invention will become apparent from the following descriptions given in conjunction with the accompanying drawings, in which.

DETAILED DESCRIPTION OF THE INVENTION

Figure 1:
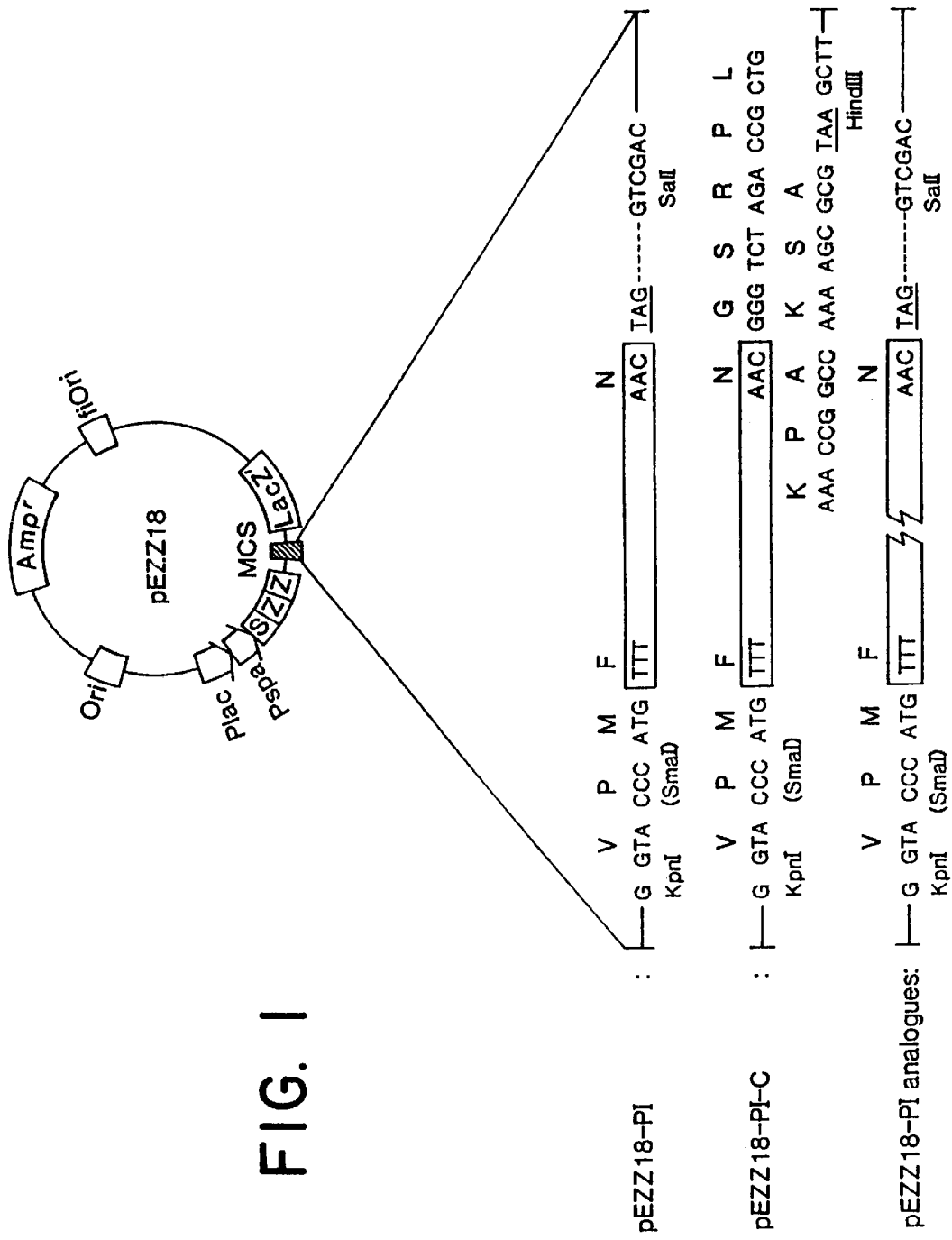
FIG. 1 is a schematic diagram of secretion vectors, pEZZ18-PI, pEZZ18-PI-C and pEZZ18-PI analogues.

Based on the facts that: the staphylococcal protein A(SPA) fusion expression/secretion system has been sucessfully employed in the secretion of human insulin-like growth factor I(hIGFI) in *E. coli*, and human proinsulin and hIGFI have a high similarity in amino acid sequence and three-dimensional structures, the inventors attempted to apply the SPA system to the secretion of proinsulin.

To see whether modification of the proinsulin, in a relation to hIGFI, has any effect on the export of proinsulin, the inventors first constructed a proinsulin secretion vector, pEZZ18-PI, which is expressed under the SPA promoter, by inserting the proinsulin gene into pEZZ18 vector. Expression and export of ZZ-proinsulin was analyzed by Coomassie blue staining of IgG-purified proteins by Western blotting, and by insulin RIA. Since the exported ZZ-proinsulin and its analogues appear to be intact and the band intensities from Coomassie blue staining and Western blotting were correlated with the amounts calculated by insulin RIA, insulin RIA was employed for quantization of relative amounts of exported proinsulin. It was found that secretion of the proinsulin into the medium(50–100 μg/l) was almost negligible, while the amount of proinsulin in the periplasmic extract(2.1 mg/l) was significantly higher than that in the medium. However, the major portion of the expressed proinsulin was found in the intracellular preparation, as compared to the amounts detected in the periplasmic space or in the medium. These results suggest that: there is little degradation of the expressed ZZ-proinsulin at the intracellular level and transcription and translation take place efficiently, while the low secretion yield may result from a low translocation efficiency of the expressed protein.

To see whether the additional carboxy terminal peptide has any effect on the export yield of ZZ-proinsulin, the inventors inserted the carboxy terminal peptide gene of hIGFI into ZZ-proinsulin vector to construct pEZZ18-PI-C. The inventors found that the export yield of proinsulin using this vector was lower than that using pEZZ18-PI, although the expression yield in the cells was significantly higher than that of ZZ-proinsulin. Most of the synthesized proinsulin was located in the cytoplasmic space rather than in the periplasmic space or in the medium, indicating that the addition of the peptide from the carboxy terminal end of hIGFI to the carboxy terminal end of ZZ-proinsulin causes a decrease in the export of ZZ-proinsulin rather than an increase.

To see whether the presence of a shorter connecting peptide has an effect on the export yield of proinsulin, the inventors constructed additional vectors containing connecting peptides of various sizes, i.e., pEZZ18-PI analogues, by sequentially deleting the connecting peptide region of proinsulin. Most of the vectors tested with different sizes of connecting peptides revealed an export of proinsulin similar to, or lower than, that using the ZZ-proinsulin vector. However, some vectors which contained a connecting peptide similar in size to that of hIGFI or which had most of the connecting peptide eliminated, showed a significant increase in the export yield of proinsulin in the periplasmic space (over 25-fold).

According to the present invention, it is clearly demonstrated that: the length of the connecting peptide region plays a critical role in the export of proinsulin; and, the highest export yield of proinsulin can be obtained when the connecting peptide region of the proinsulin is similar in size to that of hIGFI, or when most of the connecting peptide region of the proinsulin is deleted.

In describing the modification mode of the proinsulin, the term "connecting peptide region" is employed to mean a wide range of amino acid sequence comprising the connecting peptide of the proinsulin therein, as definitely described in Table 1.

Further, in describing amino acids constituting the connecting peptide region, one-letter symbols abbreviated by the IUPAC-IUB standards are employed as followings:

| Amino acid | Symbol |
|---|---|
| Alanine | A |
| Arginine | R |
| Asparagine | N |
| Aspartic aicd | D |
| Cysteine | C |
| Glutamine | Q |
| Glutamic acid | E |
| Glycine | G |
| Histidine | H |
| Isoleucine | I |
| Leucine | L |
| Lysine | K |
| Methionine | M |
| Phenylalanine | F |
| Proline | P |
| Serine | S |
| Threonine | T |
| Tryptophan | W |
| Tyrosine | Y |
| Valine | V |

The present invention is further illustrated in the following examples, which should not be taken to limit the scope of the invention.

EXAMPLE 1

Construction of secretion vectors

The human proinsulin gene containing a 5'-ATG and a 3'-HindIII site(see: Kang, Y. et al., Biotechnol. Lett., 43:755–760(1991)) was first isolated from pTZ18-PI(see: Eun, H. M. et al., Biotech., 7:506–510(1989)) by XbaI digestion, mung bean nuclease digestion, end filling with Klenow, and HindIII digestion. A secretion vector for ZZ-proinsulin(Z-an analogue of the B domain of protein A) which is expressed under staphylococcal protein A(SPA) promoter and may be translocated by the general secretion pathway through the signal sequence of SPA, was constructed by inserting the human proinsulin gene into the SmaI/HindIII site of plasmid pEZZ18(Pharmacia LKB Biotechnology, U.S.A.).

To construct pEZZ18-PI-C, the proinsulin gene was amplified by polymerase chain reaction(PCR) with 5'-forward primer(5'-ATGTTTGTGAACCAACACCTG-3', SEQ ID NO:1) and modified 3'-backward primer (5'-GGTCTAGACCCGTTGCAGTAGTTCTCCAG-3', SEQ ID NO:2). PCR was carried out at 92° C., 54° C. and 72° C. for denaturation, annealing, and synthesis, with 30 cycles. The amplified PCR product, after Klenow processing and XbaI digestion, was subcloned into SmaI and XbaI sites of pEZZ18. Then, the oligonucleotides for Pro-Leu-Lys-Pro-Ala-Lys-Ser-Ala SEQ ID NO:14(carboxy terminal sequence of hIGFI) as followings were annealed and inserted into XbaI/HindIII site of pEZZ18-PI:

5,-CTAGACCGCTGAAACCGGCCAAAAGCGCGTA-3'(SEQ ID NO:3)

5,-AGCTTACGCGCTTTTGGCCGGTTTCAGCGGT-3' (SEQ ID NO:4)

To construct pEZZ18-PI vectors containing various sizes of the connecting peptide region, pEZZ18-PI was linearized by cutting with ApaI, the site which is in the middle of the connecting peptide region. Each end of the pEZZ18-PI was sequentially degraded by treatment with slow Bal31 exonuclease (International Biotechnologies, U.S.A.). A battery of 100 pEZZ18-PI analogues was constructed by end filling with Klenow fragment, and recirculation with $T_4$ DNA ligase.

Schematic diagram of the above secretion vectors, i.e., pEZZ18-PI, pEZZ18-PI-C and pEZZ18-PI analogues, is depicted in FIG. 1. As shown in FIG. 1, proinsulin gene is inserted into the multi-cloning site(MCS) of pEZZ18. Proinsulin gene is denoted by rectangular box, and nucleotide sequence and peptide sequence near proinsulin gene are shown for each vector; and, the termination codon is underlined(Amp$^r$, gene for ampicillin resistance; Ori, replication origin of pMBL; f10ri, replication origin of f1 phage; Plac, promoter of lactose operon; Pspa, promoter of staphylococcal protein A gene; S, signal sequence of SPA; Z, an analogue of B domain of protein A; and, LacZ, fragment of β-galactosidase).

EXAMPLE 2

DNA sequencing

The DNA sequence was determined using Sanger's dideoxy DNA sequencing method(see: Sanger, F., Science, 214:1205–1210 (1981)). A double stranded plasmid was used directly for the sequencing template. The oligonucleotide(ATGTTTGTGAACCAACACCTG, SEQ ID NO:1) covering the N-terminal region of proinsulin was used as a sequencing primer. The sequencing procedure followed the protocol supplied with the Sequenase DNA sequencing kit(United State Biochemical Co., U.S.A.).

EXAMPLE 3

Expression and analysis of proinsulin

E. coli HB101 harbouring pEZZ18-PI, pEZZ18-PI-C and pEZZ18-PI analogues prepared in Example 1, were grown in 2YT medium containing 50 μg/ml of ampicillin. Cells were grown at 37° C. and harvested when the cultures reached the late log growth phase(8–10 h). The cells were harvested by centrifugation(12000 rpm, 1 min) and lysed directly in SDS-lysis buffer(5% sodiumdodecylsulfate, 75 mM Tris-HCl(pH 6.8)) in preparation for protein gel electrophoresis. To separate periplasmic protein, harvested cells were resuspended in sucrose solution (25% sucrose, 0.3M Tris-HCl(pH 8.0), 0.5 mM MgCl$_2$1 mM EDTA) and left at room temperature for 10 min. Periplasmic protein was then extracted by placing the cells in cold 0.5 mM MgCl$_2$ for 10 min and centrifugal separation(osmotic extraction method).

For Coomasie blue staining, the extracted proteins were isolated by IgG affinity chromatography(Pharmacia, U.S.A.). Active fractions were eluted by low pH buffer(0.5M acetic acid, pH 3.5) and concentrated by TCA precipitation. The proteins were separated on 10% PAGE and stained with 0.1% Coomassie blue solution.

For Western blotting, the extracted proteins were concentrated by adding an equal volume of 10% trichloroacetic acid(TCA) and leaving the mixture in the cold room for several hours. The concentrated proteins were fractionated by 10–15% polyacrylamide gel electrophoresis(PAGE) (see: Laemmli, U. K., Nature, 227:680–685(1970)). Fractionated proteins were transferred to a nitrocellulose membrane(see: Tobin, H., et al., Proc. Natl. Acad. Sci., USA, 76:4350–4354 (1979)) and immunostained by insulin A-chain specific monoclonal antibody (AE9D6)(see: Schroer, J. A. et al., Eur. J. Immunol., 13:693–700(1983)) as the first antibody and alkaline phosphatase conjugated anti-mouse IgG antibody as the secondary antibody. Positive bands were detected by bromochloroindoyl phosphate (BCIP, Sigma Chemical Co., U.S.A.) and nitroblue tetrazolium (NBT, Sigma Chemical Co., U.S.A.) staining.

Quantitative analysis of proinsulin or its analogues was carried out by radioimmunoassay(RIA) for insulin(see: Yoon, J. W. et al., Nature, 264:178–180(1976)). Periplasmic protein was extracted by osmotic extraction and diluted 10–100-fold with phosphate-buffered saline(PBS). The procedure for insulin RIA was as follows: Serially diluted samples were mixed with [$^{125}$I]insulin and insulin antibody (produced in guinea pigs). [$^{125}$I]insulin and insulin antibody complex were removed by anti-guinea pig IgG antibody and counted using a γ-counter(Rack-gamma, LKB, Sweden). The amount of insulin was calculated on the basis of a standard curve.

EXAMPLE 4

Expression and export of ZZ-proinsulin

After transformation of the secretion vector, pEZZ18-PI prepared in Example 1, into E. coli HB101, ZZ-proinsulin secreted into the medium and ZZ-proinsulin exported into the periplasmic extract(ZZ-PI) were measured respectively, by the aid of insulin RIA technique. The amount of proinsulin secreted into the medium was about 50–100 μg/l. However, the amount of proinsulin(2.1 mg/l) in the periplasmic extract was significantly higher than that in the medium, while the total amount of exported proinsulin was lower than that produced by the intracellular expression system.

To determine which step is critical for the export of ZZ-proinsulin, the expressed ZZ-proinsulin in the cytoplasmic extract(free of the periplasmic protein) and that in the periplasmic proteins were compared by Western blotting technique. E. coli HB101 cells harbouring vector pEZZ18-PI were harvested 10 hours after inoculation. Periplasmic protein and cellular protein were separeated by osmotic shock extraction. Total protein, cellular protein and periplasmic protein were separated on 10–15% discontinuous PAGE under non-reducing conditions, respectively. Immunoreactive bands were detected by Western blotting.

Figure 2:
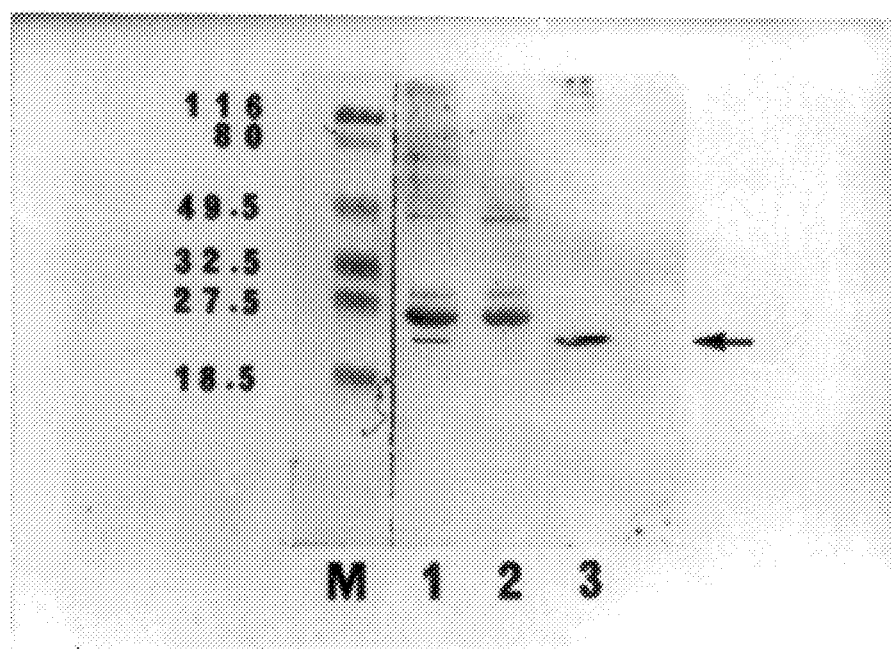
FIG. 2 is a photograph showing the results of Western blotting of ZZ-proinsulin.

The major portion of the expressed proinsulin was found in the intracellular preparation, while a minor portion of the expressed protein existed in the periplasmic space(see: FIG. 2). In FIG. 2, an arrow denotes exported ZZ-PI(MW: 25K); M represents pre-stained molecular weight marker; and, lanes 1, 2 and 3 represent total protein, cellular protein and periplasmic extracts from pEZZ18-PI, respectively. This result indicated that transcription and translation took place efficiently and there was little intracellular degradation of the expressed ZZ-proinsulin. Accordingly, it is concluded that the low export may result from a low translocation efficiency of the expressed protein.

EXAMPLE 5

Effect of carboxy terminal peptide on export of ZZ-proinsulin

There are structural differences in the carboxy terminal peptide region between proinsulin and hIGFI. For example, hIGFI has an additional peptide in the carboxy terminal end compared to human proinsulin(see: Humbell, R. E., Eur. J. Biochem., 190:445–462(1990)). To see whether this peptide has any effect on the export yield of ZZ-proinsulin, the inventors synthesized an oligonucleotide encoding the carboxy terminal peptide of hIGFI, and inserted it at the carboxy terminal end of the proinsulin gene. Then, the inventors modified the carboxy terminal end of the proinsulin using a 3'-backward primer to introduce a chemical cleavage site for hydroxylamine (Asn/Gly) (see: Uhlen, M. et al., Methods Enzymol., 188:129–143(1991)) and a restriction site for XbaI, and inserted a sequence similar to the carboxy terminal end of hIGFI into the ZZ-proinsulin vector named pEZZ18-PI-C.

Figure 3:
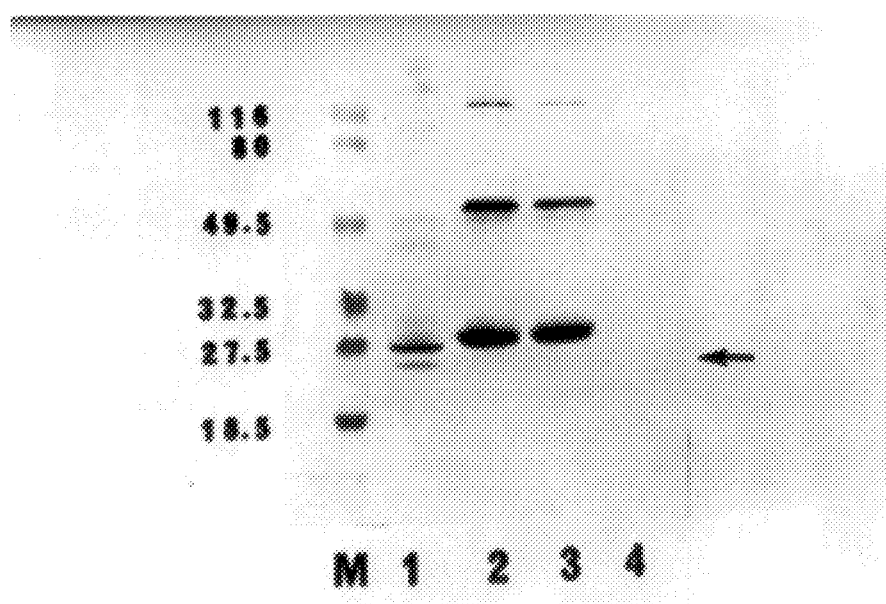
FIG. 3 is a photograph showing the result of Western blotting of exported proinsulin accompanied by hIGFI carboxy terminal peptide.

All of the expressed ZZ-proinsulin-C were detected in the cytoplasmic space with an expression yield significantly higher than that of ZZ-proinsulin. However, the exported ZZ-proinsulin-C in the periplasmic space and the secreted ZZ-proinsulin-C in the medium were under the level detectable by Western blotting(see: FIG. 3) and RIA as well; and, most of the synthesized proinsulin were located in the cytoplasmic space rather than in the periplasmic space or in Human insulin-like growth factor has a shorter peptide in the connecting peptide region than does proinsulin(see: Table 1).

TABLE 1

Amino acid sequences of ZZ-proinsulin analogues and export yield of these clones

| Clones | Amino acid sequence of ZZ-proinsulins[a] | Export yield (mg/l)[b] |
|---|---|---|
| pEZZ18-PI/ HB101 | ZZ[c] — (VDANSSSVP(— B[d] — (R — R) — C[e] — (K — R) — A[f] SEQ. ID NO: 15 | 2.1 |
| pEZZ18-PI-C/ HB101 | ZZ[c] — (VDANSSSVP) — B[d] — (R — R) — C[e] — (K — R) — A[f] — (GSRPLKPAKSA) SEQ ID NO: 16 | |
| pEZZ18-PI analogues/ HB101 | ——B[d]—(RR)————C[e]—————(KR)—A[f]— | |
| 1 | — FFYTPKT — (RR) — E - - - - - - -LQPLALEGSLQ — (KR) — GIVE - SEQ ID NO: 17 | — |
| 2 | — FFYTPKT — (R ) - - - - - - - - - - - - - - - - - ( R) — GIVE - SEQ ID NO: 18 | — |
| 3 | — F - - - - - - - - - - - - - - - - - - - - SLQ — (KR) — GIVE - SEQ ID NO: 19 | — |
| 4 | — FFYTP - - - - - - - - - - - - - - - - - - - - - - - - - IVE - SEQ ID NO: 20 | — |
| 5 | — FFYTPKT — (RR) — EAEDLQVGQVE - - - - - GSLQ — (KR) — GIVE - SEQ ID NO: 21 | 1.5 |
| 6 | — FFYTPKT — (RR) — EAEDLQVG - - - - - LALEGSLQ — (KR) — GIVE - SEQ ID NO: 22 | 2.3 |
| 7 | — FFYTPKT — (RR) — EA - - - - - - - - - - GSLQ — (KR) — GIVE - SEQ ID NO: 23 | 3.6 |
| 8 | — FFYTP — EGSLQ — (KR) - - - - - - - - - - - - - - - - - - GIVE - SEQ ID NO: 24 | 4.1 |
| 9 | — FFYTPKT — (RR) — EAEDQ - - - - - - - - - - GSLQ-(KR) — GIVE - SEQ ID NO: 10 | 5.5 |
| 10 | — FFYTPKT — (RR) — EAEDLQVGQVE - - - - - - - - - - - - - - - GIVE - SEQ. ID NO: 11 | 48.7 |
| 11 | — FFYTPKT — (RR) — E - - - - - - - - - - - - - - - - - - - - GIVE - SEQ ID NO: 12 | 53.1 |
| 12 | — FFYTPKT - - - - - - - - - - - - - - - - - - - - - - - - - - GIVE - SEQ ID NO: 13 | 58.2 |
| pEZZ18-hIGFI/ HB101[g] | — FYFNKPT - - - GYGSSSRRAPT - - - - - - - - - - - - GIVD - SEQ ID NO: 25 | 75.0 |

[a]Amino acid sequence was deduced from DNA sequence. DNA sequence of connecting peptide region was determined by double stranded dideoxy DNA sequencing using an oligonucleotide (TTTGTGAACCAACACCTGTGC, SEQ ID NO: 5) covering the N-terminal region of proinsulin as the sequencing primer.
[b]Quantity of exported protein as determined by insulin RIA. Periplasmic protein was extracted by osmotic extraction. The quantity was determined by RIA. The amount of each ZZ-proinsulin analogue was calculated by multiplying 2.5 times the value obtained by insulin RIA, due to the difference in cross reactivity between insulin and proinsulin (cross reactivity of proinsulin is about 40% that of insulin). In addition, the resulting value was gain multiplied by 2.5–3.5, depending on the ratio of the molecular weight of the ZZ-proinsulin analogue to that of insulin.
[c]Amino acid sequence of Z: VDNKFNKEQQNAFYEILHLPNLNEEQRNAFIQSLKD DQSANLLAEAKKLNDAQAPK (SEQ ID NO: 6).
[d]Amino acid sequence of B-chain of human insulin: FVNQHLCGSHLVEALYLV CGERGFFYTPKT (SEQ ID NO: 7).
[e]Amino acid sequence of connecting peptide of human proinsulin: EAEDLQVGQVELGGGPGAGSLQPLALEGSLQ (SEQ ID NO: 8).
[f]Amino acid sequence of A-chain of human proinsulin: GIVEQCCTSICSLYQLENYCN (SEQ ID NO: 9).
[g]Amino acid sequence of the connecting peptide region in human insulin-like growth factor I and its secretion yield.

the medium, indicating that the addition of the peptide of the carboxy terminal end of hIGFI to the carboxy terminal end of ZZ-proinsulin causes a decrease in the export of ZZ-proinsulin rather than an increase.

As shown in FIG. 3, total protein, cellular protein(free of periplasmic protein) and periplasmic protein(ZZ-PI-C) were detected by Western blotting. The amount of protein equivalent to that extracted from 25 μl of cultured *E. coli* HB101 cells was loaded on each lane. An arrow represents exported ZZ-PI; M represents pre-stained molecular weight marker; and, lane 1 represents total protein extract from pEZZ18-PI, lanes 2, 3 and 4 represent total protein, cellular protein and periplasmic protein extracts from pEZZ18-PI-C, respectively. This result indicated that the addition of a peptide of the carboxy terminal end of hIGFI to the carboxy terminal end of proinsulin blocked the translocation of ZZ-proinsulin rather than accelerating it, suggesting that the addition of the carboxy terminal end of hIGF does not improve the export yield of proinsulin in this system.

EXAMPLE 6
Effect of sequential deletion of connecting peptide region on export of ZZ-proinsulin In order to investigate whether or not the presence of this shorter peptide in the connecting peptide has an effect on the export yield of proinsulin, the inventors constructed additional vectors containing connecting peptide regions of various sizes, i.e., pEZZ18-PI analogues, as follows: pEZZ18-PI was cleaved with ApaI and the gene for the connecting peptide was sequentially degraded by slow Bal31 exonuclease treatment. A battery of 100 clones containing various sizes of connecting peptides, was constructed and tested for the export of proinsulin by Western blotting.

Figure 4:
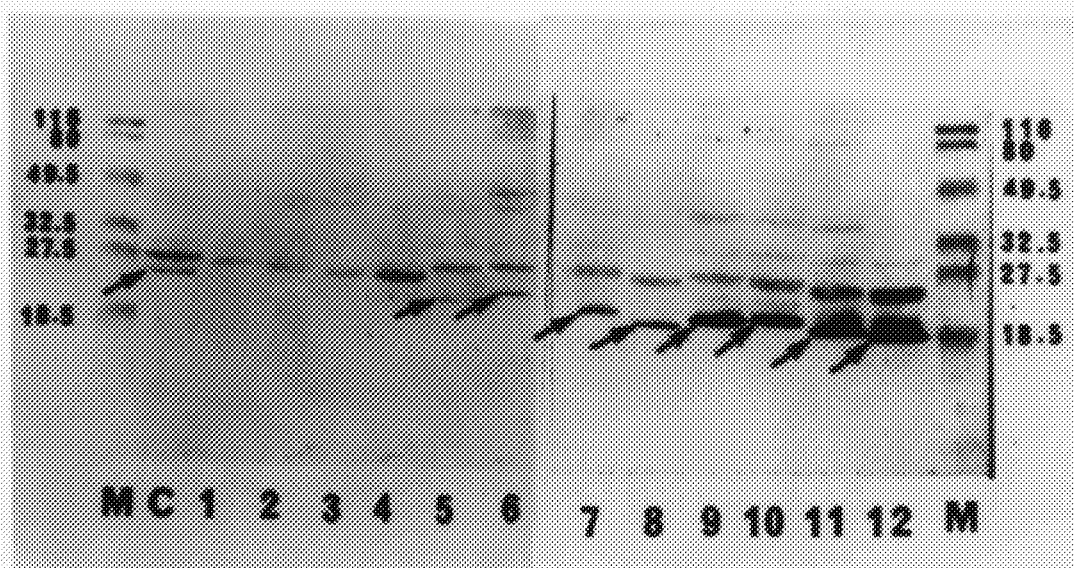
FIG. 4 is a photograph showing the result of Western blotting of exported proinsulin whose connecting peptide is sequentially deleted; and, FIG. 5 is a photograph showing the result of Coomassie blue staining of exported ZZ-proinsulin and its analogues.

FIG. 4 shows Western blots of total protein extract of ZZ proinsulin analogues(clones 1–12) containing different sizes of connecting peptide. Arrows represent the exported form of ZZ-proinsulin analogues; M represents pre-stained molecular weight markers; and, C represents total protein extract from pEZZ18-PI from cultured *E. coli* HB101 cells. As shown in FIG. 4, most of the clones tested revealed an export similar to (clones 5, 6, 7 and 8) or lower than(clones 1, 2, 3 and 4) that of ZZ-proinsulin. Furthermore, most of the clones that showed a lower export, also showed a lower expression of the precursor form of proinsulin in the cytoplasm(e.g., clones 1, 2 and 3). In contrast, some clones (e.g., clone 4) showed a higher expression of the precursor form of proinsulin, although exported proinsulin was not detected. The expression and export pattern of this clone were the same as that of the pEZZ18-PI-C clone. Other clones(e.g., clones 9, 10, 11 and 12) showed a significant increase in export yield compared to that of the clones described above and that of ZZ-proinsulin.

Figure 5:
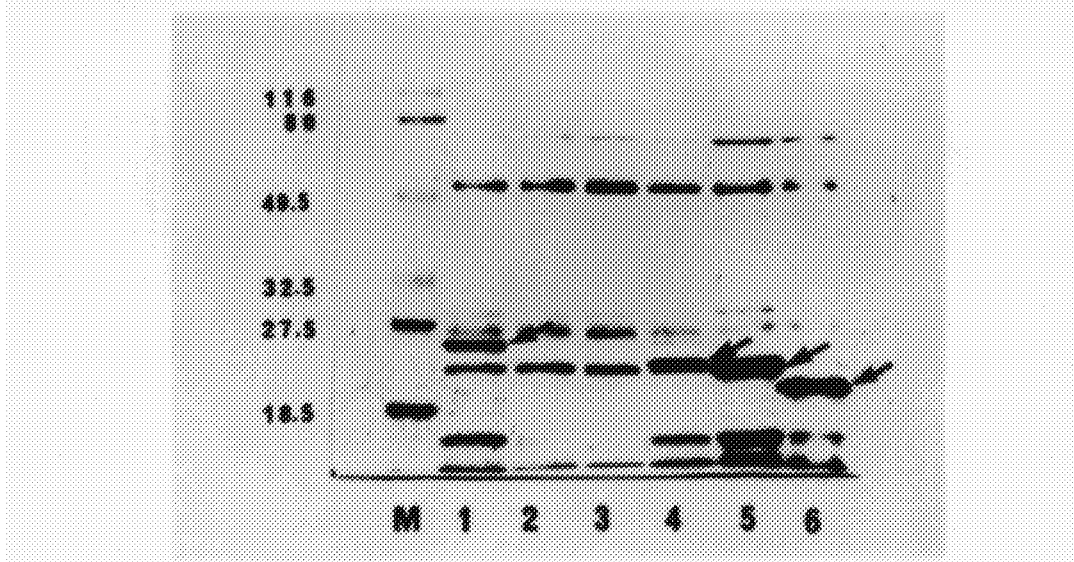

The inventors compared these clones in regard to the size of the connecting peptide region, and found that they contained a connecting peptide similar in size to that of hIGF (e.g., clones 9 and 10) or had most of the connecting peptide eliminated(e.g., clones 11 and 12). Sequence analysis of these clones revealed that the presence or absence of two or three amino acids, creating connecting peptides of different lengths, resulted in dramatic changes in the export yield of proinsulin (see: Table 1—e.g., clone 4 compared to clone 12; clone 2 compared to clone 11; clone 7 compared clone 9). FIG. 5 shows the result of Coomassie blue staining of exported ZZ-proinsulin and its analogues. IgG affinity chromatography-purified proteins equivalent to 1.0 ml culture were separated on 10% PAGE, and stained with Coomassie blue. Arrows show the ZZ proinsulin and its analogues; M represents pre-stained molecular weight marker; lanes 1 and 2 represent clones pEZZ18-PI and pEZZ18-PI-C; and, lanes 3, 4, 5 and 6 represent clones 4, 7, 9 and 12 on FIG. 4, respectively. This result indicated that the length of the connecting peptide region plays a critical role in the export of proinsulin, thus the presence or absence of two or three amino acids of the connecting peptide causes dramatic changes in the export of proinsulin into the periplasmic space.

As clearly demonstrated and illustrated as above, the present invention provides a method for manufacture of proinsulin with high export yield by modifying the connecting peptide region of the proinsulin. According to the method of the present invention, the highest export yield of proinsulin can be obtained, when its connecting peptide region is similar in size to that of hIGFI or when most of the connecting peptide region of the proinsulin is deleted.

What is claimed is:

1. A method for increasing the export yield of proinsulin from bacterial cells expressing proinsulin, which comprises modifying a proinsulin secretion vector such that the connecting peptide region of the proinsulin has the amino acid sequence RREAEDQGSLQKR, which are residues 8–10 of SEQ. ID. NO. 10 and producing the proinsulin in bacterial cells.

2. A method for increasing the export yield of proinsulin from bacterial cells expressing proinsulin, which comprises modifying a proinsulin secretion vector such that the connecting peptide region of the proinsulin has the amino acid sequence RREAEDLQVGQVE, which are residues 8 to 20 of SEQ ID NO: 11, and producing the proinsulin in bacterial cells.

3. A method for increasing the export yield of proinsulin from bacterial cells expressing proinsulin, which comprises modifying a proinsulin secretion vector such that the connecting peptide region of the proinsulin has the amino acid sequence RRE, which are residues 8 to 10 of SEQ ID NO:12, and producing the proinsulin in bacterial cells.

4. A method for increasing the export yield of proinsulin from bacterial cells expressing proinsulin, which comprises the step of deleting the connecting peptide region of the proinsulin, and producing the proinsulin in bacterial cells.

* * * * *

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA to mRNA ( v i ) ORIGINAL SOURCE:
        ( A ) ORGANISM: Homo sapiens ( v i i ) IMMEDIATE SOURCE:
        ( B ) CLONE: PROINSULIN 5'PRIMER ( x i ) SEQUENCE DESCRIPTION: SEQ ID NO:1:

ATGTTTGTGA ACCAACACCT G        21

( 2 ) INFORMATION FOR SEQ ID NO:2:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA to mRNA ( v i ) ORIGINAL SOURCE:
        ( A ) ORGANISM: Homo sapiens ( v i i ) IMMEDIATE SOURCE:
        ( B ) CLONE: PROINSULIN 3'PRIMER ( x i ) SEQUENCE DESCRIPTION: SEQ ID NO:2:

GGTCTAGACC CGTTGCAGTA GTTCTCCAG        29

( 2 ) INFORMATION FOR SEQ ID NO:3:

( i ) SEQUENCE CHARACTERISTICS:
        ( A ) LENGTH: 31 base pairs ( B ) TYPE: nucleic acid
( C ) STRANDEDNESS: single
( D ) TOPOLOGY: linear ( i i ) MOLECULE TYPE: cDNA to mRNA ( v i ) ORIGINAL SOURCE:
( A ) ORGANISM: Homo sapiens ( v i i ) IMMEDIATE SOURCE:
( B ) CLONE: C-TERM HIGFI OLIGO I ( x i ) SEQUENCE DESCRIPTION: SEQ ID NO:3:

CTAGACCGCT GAAACCGGCC AAAAGCGCGT A                                              31

( 2 ) INFORMATION FOR SEQ ID NO:4:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: cDNA to mRNA ( v i ) ORIGINAL SOURCE:
( A ) ORGANISM: Homo sapiens ( v i i ) IMMEDIATE SOURCE:
( B ) CLONE: C-TERM HIGFI OLIGO II ( x i ) SEQUENCE DESCRIPTION: SEQ ID NO:4:

AGCTTACGCG CTTTTGGCCG GTTTCAGCGG T                                              31

( 2 ) INFORMATION FOR SEQ ID NO:5:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: cDNA to mRNA ( v i ) ORIGINAL SOURCE:
( A ) ORGANISM: Homo sapiens ( v i i ) IMMEDIATE SOURCE:
( B ) CLONE: PPINSULIN- N-TERM SEQ PRIMER ( x i ) SEQUENCE DESCRIPTION: SEQ ID NO:5:

TTTGTGAACC AACACCTGTG C                                                        21

( 2 ) INFORMATION FOR SEQ ID NO:6:

( i ) SEQUENCE CHARACTERISTICS:
( A ) LENGTH: 56 amino acids
( B ) TYPE: amino acid
( C ) STRANDEDNESS: Not Relevant
( D ) TOPOLOGY: Not Relevant ( i i ) MOLECULE TYPE: protein ( v i ) ORIGINAL SOURCE:
( A ) ORGANISM: Homo sapiens ( v i i ) IMMEDIATE SOURCE:
( B ) CLONE: Z ( x i ) SEQUENCE DESCRIPTION: SEQ ID NO:6:

Val Asp Asn Lys Phe Asn Lys Glu Gln Gln Asn Ala Phe Tyr Glu Ile
1               5                   10                  15

-continued

```
Leu  His  Leu  Pro  Asn  Leu  Asn  Glu  Glu  Gln  Arg  Asn  Ala  Phe  Ile  Gln
               20                  25                       30

Ser  Leu  Lys  Asp  Asp  Gln  Ser  Ala  Asn  Leu  Leu  Ala  Glu  Ala  Lys  Lys
               35                  40                       45

Leu  Asn  Asp  Ala  Gln  Ala  Pro  Lys
               50                  55
```

( 2 ) INFORMATION FOR SEQ ID NO:7:

( i ) SEQUENCE CHARACTERISTICS:
    ( A ) LENGTH: 30 amino acids
    ( B ) TYPE: amino acid
    ( C ) STRANDEDNESS: Not Relevant
    ( D ) TOPOLOGY: Not Relevant ( i i ) MOLECULE TYPE: protein ( v i ) ORIGINAL SOURCE:
    ( A ) ORGANISM: Homo sapiens ( v i i ) IMMEDIATE SOURCE:
    ( B ) CLONE: INSULIN B ( x i ) SEQUENCE DESCRIPTION: SEQ ID NO:7:

```
Phe  Val  Asn  Gln  His  Leu  Cys  Gly  Ser  His  Leu  Val  Glu  Ala  Leu  Tyr
 1                   5                       10                      15

Leu  Val  Cys  Gly  Glu  Arg  Gly  Phe  Phe  Tyr  Thr  Pro  Lys  Thr
               20                  25                       30
```

( 2 ) INFORMATION FOR SEQ ID NO:8:

( i ) SEQUENCE CHARACTERISTICS:
    ( A ) LENGTH: 31 amino acids
    ( B ) TYPE: amino acid
    ( C ) STRANDEDNESS: Not Relevant
    ( D ) TOPOLOGY: Not Relevant ( i i ) MOLECULE TYPE: peptide ( v i ) ORIGINAL SOURCE:
    ( A ) ORGANISM: Homo sapiens ( v i i ) IMMEDIATE SOURCE:
    ( B ) CLONE: PROINSULIN CONNECTING PEPTIDE ( x i ) SEQUENCE DESCRIPTION: SEQ ID NO:8:

```
Glu  Ala  Glu  Asp  Leu  Gln  Val  Gly  Gln  Val  Glu  Leu  Gly  Gly  Gly  Pro
 1                   5                       10                      15

Gly  Ala  Gly  Ser  Leu  Gln  Pro  Leu  Ala  Leu  Glu  Gly  Ser  Leu  Gln
               20                  25                       30
```

( 2 ) INFORMATION FOR SEQ ID NO:9:

( i ) SEQUENCE CHARACTERISTICS:
    ( A ) LENGTH: 21 amino acids
    ( B ) TYPE: amino acid
    ( C ) STRANDEDNESS: Not Relevant
    ( D ) TOPOLOGY: Not Relevant ( i i ) MOLECULE TYPE: protein ( v i ) ORIGINAL SOURCE:
    ( A ) ORGANISM: Homo sapiens ( v i i ) IMMEDIATE SOURCE:
    ( B ) CLONE: PROINSULIN A CHAIN ( x i ) SEQUENCE DESCRIPTION: SEQ ID NO:9:

```
Gly  Ile  Val  Glu  Gln  Cys  Cys  Thr  Ser  Ile  Cys  Ser  Leu  Tyr  Gln  Leu
 1                   5                       10                      15
```

Glu Asn Tyr Cys Asn
                 20

( 2 ) INFORMATION FOR SEQ ID NO:10:

( i ) SEQUENCE CHARACTERISTICS:
                  ( A ) LENGTH: 24 amino acids
                  ( B ) TYPE: amino acid
                  ( C ) STRANDEDNESS: Not Relevant
                  ( D ) TOPOLOGY: Not Relevant ( i i ) MOLECULE TYPE: peptide ( v i ) ORIGINAL SOURCE:
                  ( A ) ORGANISM: Homo sapiens ( v i i ) IMMEDIATE SOURCE:
                  ( B ) CLONE: CONN PEPTIDE ( x i ) SEQUENCE DESCRIPTION: SEQ ID NO:10:

Phe Phe Tyr Thr Pro Lys Thr Arg Arg Glu Ala Glu Asp Gln Gly Ser
        1               5                   10                  15

Leu Gln Lys Arg Gly Ile Val Glu
                 20

( 2 ) INFORMATION FOR SEQ ID NO:11:

( i ) SEQUENCE CHARACTERISTICS:
                  ( A ) LENGTH: 24 amino acids
                  ( B ) TYPE: amino acid
                  ( C ) STRANDEDNESS: Not Relevant
                  ( D ) TOPOLOGY: Not Relevant ( i i ) MOLECULE TYPE: peptide ( v i ) ORIGINAL SOURCE:
                  ( A ) ORGANISM: Homo sapiens ( v i i ) IMMEDIATE SOURCE:
                  ( B ) CLONE: CONN PEPTIDE ( x i ) SEQUENCE DESCRIPTION: SEQ ID NO:11:

Phe Phe Tyr Thr Pro Lys Thr Arg Arg Glu Ala Glu Asp Leu Gln Val
        1               5                   10                  15

Gly Gln Val Glu Gly Ile Val Glu
                 20

( 2 ) INFORMATION FOR SEQ ID NO:12:

( i ) SEQUENCE CHARACTERISTICS:
                  ( A ) LENGTH: 14 amino acids
                  ( B ) TYPE: amino acid
                  ( C ) STRANDEDNESS: Not Relevant
                  ( D ) TOPOLOGY: Not Relevant ( i i ) MOLECULE TYPE: peptide ( v i ) ORIGINAL SOURCE:
                  ( A ) ORGANISM: Homo sapiens ( v i i ) IMMEDIATE SOURCE:
                  ( B ) CLONE: CONN PEPTIDE ( x i ) SEQUENCE DESCRIPTION: SEQ ID NO:12:

Phe Phe Tyr Thr Pro Lys Thr Arg Arg Glu Gly Ile Val Glu
        1               5                   10

( 2 ) INFORMATION FOR SEQ ID NO:13:

( i ) SEQUENCE CHARACTERISTICS:

(A) LENGTH: 11 amino acids
(B) TYPE: amino acid
(C) STRANDEDNESS: Not Relevant
(D) TOPOLOGY: Not Relevant (ii) MOLECULE TYPE: peptide (vi) ORIGINAL SOURCE:
(A) ORGANISM: Homo sapiens (vii) IMMEDIATE SOURCE:
(B) CLONE: CONN PEPTIDE (xi) SEQUENCE DESCRIPTION: SEQ ID NO:13:

Phe Phe Tyr Thr Pro Lys Thr Gly Ile Val Glu
1               5                   10

(2) INFORMATION FOR SEQ ID NO:14:

(i) SEQUENCE CHARACTERISTICS:
(A) LENGTH: 8 amino acids
(B) TYPE: amino acid
(C) STRANDEDNESS: Not Relevant
(D) TOPOLOGY: Not Relevant (ii) MOLECULE TYPE: peptide (vi) ORIGINAL SOURCE:
(A) ORGANISM: Homo sapiens (vii) IMMEDIATE SOURCE:
(B) CLONE: C-TERM HIGFI (xi) SEQUENCE DESCRIPTION: SEQ ID NO:14:

Pro Leu Lys Pro Ala Lys Ser Ala
1               5

(2) INFORMATION FOR SEQ ID NO:15:

(i) SEQUENCE CHARACTERISTICS:
(A) LENGTH: 151 amino acids
(B) TYPE: amino acid
(C) STRANDEDNESS: Not Relevant
(D) TOPOLOGY: Not Relevant (ii) MOLECULE TYPE: protein (vi) ORIGINAL SOURCE:
(A) ORGANISM: Homo sapiens (vii) IMMEDIATE SOURCE:
(B) CLONE: PROINSULIN PEZZI8- PI (xi) SEQUENCE DESCRIPTION: SEQ ID NO:15:

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
                20                  25                  30

Ser Leu Lys Asp Asp Gln Ser Ala Asn Leu Leu Ala Glu Ala Lys Lys
            35                  40                  45

Leu Asn Asp Ala Gln Ala Pro Lys Val Asp Ala Asn Ser Ser Ser Val
        50                  55                  60

Pro Phe Val Asn Gln His Leu Cys Gly Ser His Leu Val Glu Ala Leu
65                  70                  75                  80

Tyr Leu Val Cys Gly Glu Arg Gly Phe Phe Tyr Thr Pro Lys Thr Arg
                85                  90                  95

Arg Glu Ala Glu Asp Leu Gln Val Gly Gln Val Glu Leu Gly Gly Gly
                100                 105                 110

```
            Pro   Gly   Ala   Gly   Ser   Leu   Gln   Pro   Leu   Ala   Leu   Glu   Gly   Ser   Leu   Gln
                        115                     120                           125

Lys   Arg   Gly   Ile   Val   Glu   Gln   Cys   Cys   Thr   Ser   Ile   Cys   Ser   Leu   Tyr
                        130                     135                           140

Gln   Leu   Glu   Asn   Tyr   Cys   Asn
            145                           150
```

( 2 ) INFORMATION FOR SEQ ID NO:16:

( i ) SEQUENCE CHARACTERISTICS:
        ( A ) LENGTH: 161 amino acids
        ( B ) TYPE: amino acid
        ( C ) STRANDEDNESS: Not Relevant
        ( D ) TOPOLOGY: Not Relevant ( i i ) MOLECULE TYPE: protein ( v i ) ORIGINAL SOURCE:
        ( A ) ORGANISM: Homo sapiens ( v i i ) IMMEDIATE SOURCE:
        ( B ) CLONE: PROINSULIN-PEZZ18-PI- C ( x i ) SEQUENCE DESCRIPTION: SEQ ID NO:16:

```
            Val   Asp   Asn   Lys   Phe   Asn   Lys   Glu   Gln   Gln   Asn   Ala   Phe   Tyr   Glu   Ile
            1                       5                       10                          15

Leu   His   Leu   Pro   Asn   Leu   Asn   Glu   Glu   Gln   Arg   Asn   Ala   Phe   Ile   Gln
                              20                            25                          30

Ser   Leu   Lys   Asp   Asp   Gln   Ser   Ala   Asn   Leu   Leu   Ala   Glu   Lys   Lys   Leu
                        35                            40                          45

Asn   Asp   Ala   Gln   Ala   Pro   Lys   Val   Asp   Ala   Asn   Ser   Ser   Ser   Val   Pro
                  50                            55                          60

Phe   Val   Asn   Gln   His   Leu   Cys   Gly   Ser   His   Leu   Val   Glu   Ala   Leu   Tyr
            65                            70                          75                          80

Leu   Val   Cys   Gly   Glu   Arg   Gly   Phe   Phe   Tyr   Thr   Pro   Lys   Thr   Arg   Arg
                                    85                            90                          95

Glu   Ala   Glu   Asp   Leu   Gln   Val   Gly   Gln   Val   Glu   Leu   Gly   Gly   Gly   Pro
                              100                           105                         110

Gly   Ala   Gly   Ser   Leu   Gln   Pro   Leu   Ala   Leu   Glu   Gly   Ser   Leu   Gln   Lys
                        115                           120                         125

Arg   Gly   Ile   Val   Glu   Gln   Cys   Cys   Thr   Ser   Ile   Cys   Ser   Leu   Tyr   Gln
                        130                           135                         140

Leu   Glu   Asn   Tyr   Cys   Asn   Gly   Ser   Arg   Pro   Leu   Lys   Pro   Ala   Lys   Ser
            145                           150                         155                         160

Ala
```

( 2 ) INFORMATION FOR SEQ ID NO:17:

( i ) SEQUENCE CHARACTERISTICS:
        ( A ) LENGTH: 27 amino acids
        ( B ) TYPE: amino acid
        ( C ) STRANDEDNESS: Not Relevant
        ( D ) TOPOLOGY: Not Relevant ( i i ) MOLECULE TYPE: peptide ( v i ) ORIGINAL SOURCE:
        ( A ) ORGANISM: Homo sapiens ( v i i ) IMMEDIATE SOURCE:
        ( B ) CLONE: CONN PEPTIDE ( x i ) SEQUENCE DESCRIPTION: SEQ ID NO:17:

```
            Phe   Phe   Tyr   Thr   Pro   Lys   Thr   Arg   Arg   Glu   Leu   Gln   Pro   Leu   Ala   Leu
```

```
             1               5                    10                      15
       Glu  Gly  Ser  Leu  Gln  Lys  Arg  Gly  Ile  Val  Glu
                        20                    25
```

( 2 ) INFORMATION FOR SEQ ID NO:18:

( i ) SEQUENCE CHARACTERISTICS:
        ( A ) LENGTH: 13 amino acids
        ( B ) TYPE: amino acid
        ( C ) STRANDEDNESS: Not Relevant
        ( D ) TOPOLOGY: Not Relevant ( i i ) MOLECULE TYPE: peptide ( v i ) ORIGINAL SOURCE:
        ( A ) ORGANISM: Homo sapiens ( v i i ) IMMEDIATE SOURCE:
        ( B ) CLONE: CONN PEPTIDE ( x i ) SEQUENCE DESCRIPTION: SEQ ID NO:18:

```
       Phe  Phe  Tyr  Thr  Pro  Lys  Thr  Arg  Arg  Gly  Ile  Val  Glu
       1               5                         10
```

( 2 ) INFORMATION FOR SEQ ID NO:19:

( i ) SEQUENCE CHARACTERISTICS:
        ( A ) LENGTH: 10 amino acids
        ( B ) TYPE: amino acid
        ( C ) STRANDEDNESS: Not Relevant
        ( D ) TOPOLOGY: Not Relevant ( i i ) MOLECULE TYPE: peptide ( v i ) ORIGINAL SOURCE:
        ( A ) ORGANISM: Homo sapiens ( v i i ) IMMEDIATE SOURCE:
        ( B ) CLONE: CONN PEPTIDE ( x i ) SEQUENCE DESCRIPTION: SEQ ID NO:19:

```
       Phe  Ser  Leu  Gln  Lys  Arg  Gly  Ile  Val  Glu
       1               5                    10
```

( 2 ) INFORMATION FOR SEQ ID NO:20:

( i ) SEQUENCE CHARACTERISTICS:
        ( A ) LENGTH: 8 amino acids
        ( B ) TYPE: amino acid
        ( C ) STRANDEDNESS: Not Relevant
        ( D ) TOPOLOGY: Not Relevant ( i i ) MOLECULE TYPE: peptide ( v i ) ORIGINAL SOURCE:
        ( A ) ORGANISM: Homo sapiens ( v i i ) IMMEDIATE SOURCE:
        ( B ) CLONE: CONN PEPTIDE ( x i ) SEQUENCE DESCRIPTION: SEQ ID NO:20:

```
       Phe  Phe  Tyr  Thr  Pro  Ile  Val  Glu
       1               5
```

( 2 ) INFORMATION FOR SEQ ID NO:21:

( i ) SEQUENCE CHARACTERISTICS:
        ( A ) LENGTH: 30 amino acids
        ( B ) TYPE: amino acid
        ( C ) STRANDEDNESS: Not Relevant
        ( D ) TOPOLOGY: Not Relevant (  i i  ) MOLECULE TYPE: peptide (  v i  ) ORIGINAL SOURCE:
    (  A  ) ORGANISM: Homo sapiens (  v i i  ) IMMEDIATE SOURCE:
    (  B  ) CLONE: CONN PEPTIDE (  x i  ) SEQUENCE DESCRIPTION: SEQ ID NO:21:

```
Phe Phe Tyr Thr Pro Lys Thr Arg Arg Glu Ala Glu Asp Leu Gln Val
 1               5                   10                  15
Gly Gln Val Glu Gly Ser Leu Gln Lys Arg Gly Ile Val Glu
                20                  25                  30
```

( 2 ) INFORMATION FOR SEQ ID NO:22:

(  i  ) SEQUENCE CHARACTERISTICS:
    (  A  ) LENGTH: 31 amino acids
    (  B  ) TYPE: amino acid
    (  C  ) STRANDEDNESS: Not Relevant
    (  D  ) TOPOLOGY: Not Relevant (  i i  ) MOLECULE TYPE: peptide (  v i  ) ORIGINAL SOURCE:
    (  A  ) ORGANISM: Homo sapiens (  v i i  ) IMMEDIATE SOURCE:
    (  B  ) CLONE: CONN PEPTIDE (  x i  ) SEQUENCE DESCRIPTION: SEQ ID NO:22:

```
Phe Phe Tyr Thr Pro Lys Thr Arg Arg Glu Ala Glu Asp Leu Gln Val
 1               5                   10                  15
Gly Leu Ala Leu Glu Gly Ser Leu Gln Lys Arg Gly Ile Val Glu
                20                  25                  30
```

( 2 ) INFORMATION FOR SEQ ID NO:23:

(  i  ) SEQUENCE CHARACTERISTICS:
    (  A  ) LENGTH: 21 amino acids
    (  B  ) TYPE: amino acid
    (  C  ) STRANDEDNESS: Not Relevant
    (  D  ) TOPOLOGY: Not Relevant (  i i  ) MOLECULE TYPE: peptide (  v i  ) ORIGINAL SOURCE:
    (  A  ) ORGANISM: Homo sapiens (  v i i  ) IMMEDIATE SOURCE:
    (  B  ) CLONE: CONN PEPTIDE (  x i  ) SEQUENCE DESCRIPTION: SEQ ID NO:23:

```
Phe Phe Tyr Thr Pro Lys Thr Arg Arg Glu Ala Gly Ser Leu Gln Lys
 1               5                   10                  15
Arg Gly Ile Val Glu
                20
```

( 2 ) INFORMATION FOR SEQ ID NO:24:

(  i  ) SEQUENCE CHARACTERISTICS:
    (  A  ) LENGTH: 16 amino acids
    (  B  ) TYPE: amino acid
    (  C  ) STRANDEDNESS: Not Relevant
    (  D  ) TOPOLOGY: Not Relevant (  i i  ) MOLECULE TYPE: peptide (  v i  ) ORIGINAL SOURCE:
    (  A  ) ORGANISM: Homo sapiens

```
        ( v i i ) IMMEDIATE SOURCE:
                ( B ) CLONE: CONN PEPTIDE ( x i ) SEQUENCE DESCRIPTION: SEQ ID NO:24:

Phe  Phe  Tyr  Thr  Pro  Glu  Gly  Ser  Leu  Gln  Lys  Arg  Gly  Ile  Val  Glu
        1              5                        10                       15

( 2 ) INFORMATION FOR SEQ ID NO:25:

( i ) SEQUENCE CHARACTERISTICS:
                ( A ) LENGTH: 22 amino acids
                ( B ) TYPE: amino acid
                ( C ) STRANDEDNESS: Not Relevant
                ( D ) TOPOLOGY: Not Relevant ( i i ) MOLECULE TYPE: peptide ( v i ) ORIGINAL SOURCE:
                ( A ) ORGANISM: Homo sapiens ( v i i ) IMMEDIATE SOURCE:
                ( B ) CLONE: CONN PEPTIDE ( x i ) SEQUENCE DESCRIPTION: SEQ ID NO:25:

Phe  Tyr  Phe  Asn  Lys  Pro  Thr  Gly  Tyr  Gly  Ser  Ser  Ser  Arg  Arg  Ala
        1              5                        10                       15

Pro  Thr  Gly  Ile  Val  Asp
                       20
```